United States Patent [19]
McQuigg et al.

[11] Patent Number: 5,574,180
[45] Date of Patent: Nov. 12, 1996

[54] PROCESS FOR RECOVERING PHYTIC ACID, LACTIC ACID OR INOSITOL

[75] Inventors: Donald McQuigg, Mooresville, Ind.; Charles Marston, Midland, Mich.; Gina Fitzpatrick, Indianapolis; Ernest Crowe, Beech Grove, both of Ind.; Susan Vorhies; Ramiah Murugan, both of Indianapolis, Ind.; Thomas D. Bailey, Greenwood, Ind.

[73] Assignee: Reilly Industries, Inc., Indianapolis, Ind.

[21] Appl. No.: 284,826

[22] Filed: Aug. 1, 1994

Related U.S. Application Data

[63] Continuation of Ser. No. 964,118, Oct. 21, 1992, abandoned, which is a continuation of Ser. No. 669,045, Mar. 14, 1991, abandoned.

[51] Int. Cl.$^6$ .......................... C07C 51/42; C07C 59/48; C07C 35/16; C07C 65/10
[52] U.S. Cl. .......................... 558/147; 562/586; 562/589; 568/833
[58] Field of Search .......................... 558/147; 562/586, 562/589; 568/833

[56] References Cited

U.S. PATENT DOCUMENTS

| | | | |
|---|---|---|---|
| 3,410,929 | 11/1968 | Ledding et al. | 558/147 |
| 3,591,665 | 7/1971 | Kimura et al. | 558/147 |
| 4,323,702 | 4/1982 | Kawabata et al. | 562/485 |
| 4,482,761 | 11/1984 | Chao et al. | 568/833 |
| 4,668,813 | 5/1987 | Ogawa et al. | 558/147 |
| 4,720,579 | 1/1988 | Kulprathipanja et al. | 562/580 |
| 4,851,573 | 7/1989 | Kulprathipanja et al. | 562/580 |
| 4,851,574 | 7/1989 | Kulprathipanja et al. | 562/580 |
| 4,855,494 | 8/1989 | Margureanu et al. | 562/580 |
| 4,924,027 | 5/1990 | Kulprathipanja et al. | 562/580 |
| 5,068,418 | 11/1991 | Kulprathipanja et al. | 562/580 |
| 5,096,594 | 3/1992 | Rabinowitz | 562/580 |

*Primary Examiner*—Floyd D. Higel
*Attorney, Agent, or Firm*—Woodard, Emhardt, Naughton Moriarty & McNett

[57] ABSTRACT

Described is a process for recovering phytic acid or phytic acid salt from a medium in which it is contained. This process includes contacting the medium with a solid-phase free base polymer having tertiary amine functions to adsorb the phytic acid or salt thereof. In one preferred mode, the medium to be treated also contains lactic acid, and separate fractions predominant in (i) lactic acid and (ii) phytic acid or phytic acid salt, respectively, are recovered. Also described are preferred processes for treating mediums to recover lactic acid therefrom, and a favored process for obtaining inositol directly by hydrolyzing phytic acid or phytic acid salt while adsorbed on a pyridine-containing polymer.

31 Claims, No Drawings

5,574,180

PROCESS FOR RECOVERING PHYTIC ACID, LACTIC ACID OR INOSITOL

REFERENCE TO RELATED APPLICATION

This application is a continuation of application No. 07/964,118, filed Oct. 21, 1992 now abandoned, which is a continuation of U.S. patent application Ser. No. 07/669,045, filed Mar. 14, 1991, now abandoned.

BACKGROUND

The present invention relates generally to the recovery of phytic and lactic acids from mediums in which they are contained, and to the production of inositol. More particularly, it relates to methods for adsorptive recovery of phytic acid and/or lactic acid, and also to methods for treating phytic acid or derivatives thereof to obtain inositol.

Phytic acid (inositolhexaphosphoric acid) occurs naturally in plant tissues, and, of particular commercial interest, in the seeds of many cereal grains. Generally, this phytic acid occurs as its insoluble calcium-magnesium salt, also known as "phytin". At present, commercially available phytic acid is derived largely from corn steep liquor and/or rice bran, which typically contains phytin at levels corresponding to about 2 weight % phytic acid.

In the past, phytin has been recovered from such mediums by precipitation. For example, the medium may be treated with an organic or inorganic acid to extract phytin, which can then be precipitated. Calcium compounds such as calcium hydroxide can also be used to precipitate the desired material as calcium phytate. However, in these precipitation methods, considerable cost is involved in the recovery and purification of the phytin material. Further, many undesirable waste products are often produced, and significant amounts of the target material are lost during processing.

In another facet of study in this area, adsorption/desorption processes have been proposed for recovering phytin. For example, in earlier work, W. Ledding et al. suggested a process in which steep water is passed over an ion retardation resin. See, U.S. Pat. No. 3,410,929 (1968). According to this patent, the resin contains a mixture of anionic and cationic groups. As an illustration of the type of resins to be used, the patent describes an adsorption process using Dow Chemical Company Retardation 11 A8 resin. This resin was made by polymerizing acrylic acid within the pores of a strong base resin, Dowex Resin 1. After adsorption of the phytin, the loaded resin is rinsed with water and the phytin desorbed using a salt (NaCl) solution.

Following this earlier work by Ledding et al., Ogawa et al., in U.S. Pat. No. 4,668,813, described obtaining phytin by treating a phytin-containing solution with an ion-exchange resin. As stated in the patent, the phytin-containing solution is passed through a bed of an anion-exchange resin (e.g. strong ionic base $OH^\ominus$, $CH_3COO^\ominus$, or $Cl^\ominus$ -type resins exemplified in the patent). After water wash of the phytin-loaded resin, aqueous sodium hydroxide is passed through the resin bed to thereby elute the phytin as its sodium salt, which can then be converted to phytic acid.

Phytic acid per se has many uses, for instance as a metal chelator in animal fat and vegetable oil processing, as a rust inhibitor, in the treatment of hard water, as a nutrient, etc. However, phytic acid also enjoys substantial utility as an intermediate to its corresponding alcohol. In turn, this alcohol, commonly known and referred to as inositol, has wide application in medicine, nutrition, and also as an intermediate to still other useful compounds. As to its preparation, inositol has been obtained from phytic acid by hydrolysis with water at 100° C. See, D. J. Cosgrove, "Inositol Phosphates", Elsevier, Amsterdam, 1980, p. 36. Inositol has also been obtained by hydrolysis of phytin with steam under pressure in an autoclave, See, F. A. Hoglan et al., J. Am. Chem. Soc., 1940, 62, 2397, and U.S. Pat. No. 2,112,553, as well as by hydrolysis of sodium phytate with water at elevated temperature and pressure in an autoclave. H. Ogawa et al., U.S. Pat. No. 4,668,813.

Other valuable materials also occur in mediums containing phytic acid. For instance, lactic acid occurs along with phytic acid in corn steep liquor. Lactic acid has also long been used in the food industry, in the production of confectionary products, soft drinks, beers, wines, dairy products, baby foods, jams, salad dressings, etc. Lactic acid is also used in the preparation of pharmaceuticals, cosmetics, agrichemicals, etc. Recently, there has been substantial academic and commercial interest in lactic acid as a potential raw material for producing biodegradable plastics. See, for instance, Lipinsky, E. S., and Sinclair, R. G., Chem. Eng. Prog., Aug., 26, (1986).

Commercially, lactic acid is at present produced via both synthetic and fermentation processes. The synthetic process converts lactonitrile to lactic acid, with the lactonitrile starting material being available as a byproduct in acrylonitrile production. Van Ness, J. H., "Hydroxy Carboxylic Acids," in Encyclopedia of Chemical Technology, 3rd Ed., Wiley, Volume 13, pp. 80–103 (1981). On the other hand, in traditional fermentation processes, lactic acid bacteria produce free lactic acid as they metabolize carbohydrate raw materials. As it is formed, the lactic acid is typically neutralized by an alkali such as NaOH, $NH_4OH$ or more commonly $CaCO_3$ to prevent a pH drop in the fermentation broth. Following the fermentation, the broth is acidified to convert the lactate salt to free lactic acid which is then separated from the broth. See, Buchta, K., "Lactic Acid", Biotechnology, H. Dellweg. Ed.), 3, 409 (1985). However, as has been recognized, this separation and purification is particularly cumbersome and inefficient. Atkinson, B. and Mavituna, F., Biochemical Engineering and Biotechnology Handbook, the Nature Press, N.Y. (1983). Thus, the search for new commercially attractive lactic acid sources and recoveries has continued for some time.

It is in light of this extensive background that the applicants applied themselves in an effort to address the continuing need and demand for truly convenient and effective recoveries of phytic and lactic acids, and conversions of phytic acid or derivatives thereof to inositol. Through their discoveries, the applicants have now succeeded in addressing these needs.

SUMMARY OF THE INVENTION

Accordingly, in one preferred embodiment, this invention provides a process for treating a medium to recover phytic acid or phytic acid salt (e.g. phytin) therein contained. In accordance with the invention, this process includes contacting the medium with a solid-phase free base polymer having tertiary amine functions to adsorb the phytic acid or phytic acid salt. In this manner, the phytic acid or phytic acid salt is adsorbed onto the polymer via an acid-base interaction.

This is in stark contrast to previous efforts in which the polymer adsorbent has been pre-functionalized, i.e. placed into strong ionic form, and in which the function between adsorbent and adsorbate has been one of ion-exchange. In several modes, this preferred process thus facilitates recovery of the phytic acid or phytic acid salt product in highly purified form while avoiding the need to employ and maintain highly functionalized, ion-exchange resins as in the prior art. Further, the preferred free base form polymers of this inventive process have adsorbed the phytic acid or phytic acid salt with high efficacy and have allowed convenient and advantageous recovery and desorption schemes as will be further detailed below. In one preferred mode of practicing this embodiment of the invention, the treated medium also contains lactic acid, and the process includes recovering from the resin a fraction predominant in phytic acid or phytic acid salt product and another fraction predominant in lactic acid product. This process mode thus provides excellent utilization of resources and efficient, economical processing of raw materials to win valuable products of commerce therefrom.

Another preferred embodiment of the invention provides a process for treating a medium to recover lactic acid therein contained. This process includes contacting the medium with a solid-phase free base polymer having tertiary amine functions to adsorb the lactic acid, desorbing said lactic acid by displacement on the polymer with a stronger acid, and collecting a desorbed lactic acid fraction free from any substantial contamination by the stronger acid. This preferred process enables recovery of lactic acid in desirable amount and purity. Further, up to about 70% or more of the lactic acid can be removed from the resin prior to any substantial contamination by the stronger acid, and subsequent to the desorption step the resin is conveniently regenerable.

Another preferred embodiment of the invention provides a process for treating a medium to recover lactic acid therein contained, comprising contacting the medium with a solid-phase free base polymer having pyridine groups to adsorb the lactic acid, and desorbing the lactic acid with hot water at a temperature of at least about 75° C. This embodiment of the invention capitalizes on the surprising discovery that when polymers having free base pyridine groups are used to adsorb lactic acid, the acid can be removed with unexpected efficiency by the convenient hot water treatment. This preferred process thus can minimize possible contaminants in the lactic acid product resulting from polymer leachares and/or the desorbent step. Further, post recovery isolation and purification measures occasioned by the presence of such contaminants can be largely or completely avoided.

Still another preferred embodiment of this invention provides a process for obtaining inositol. This process includes the steps of hydrolyzing phytic acid or phytic acid salt while adsorbed on a solid-phase free base polymer having pyridine functions to form inositol, and recovering the inositol so formed. In this manner, the highly useful inositol product can be obtained from the phytic acid or phytic acid salt starting material while avoiding the need to desorb the starting material as such and then subsequently react it to form the inositol. Further, the preferred pyridine polymers have proven highly stable and as well regenerable, considerations of critical importance especially when economical, commercial scale production is contemplated.

In light of the above, it can be seen that the invention provides processes enabling efficient, advantageous and economical recoveries of lactic acid and phytic acid or phytic acid salt, and production of inositol. Additional objects and advantages of the invention will become apparent upon reviewing the following description and appended claims.

DESCRIPTION OF PREFERRED EMBODIMENTS

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention pertains.

As discussed above, one preferred embodiment of this invention relates to a process for recovering phytic acid or phytic acid salt from a medium in which it is contained. In this regard, for purposes of the discussion hereafter, the use of the term "phytic acid" is meant to encompass phytic acid as well as salt derivatives thereof, e.g. phytin. Additionally, percents by weight set forth herein for phytic acid and its salt derivatives are all calculated as free phytic acid.

The medium to be treated will typically contain phytic acid up to its solubility limit, more typically up to about 40 weight %, and is advantageously an extract from a phytin-containing material, e.g. plant material such as corn, rice or wheat bran. More preferably, the medium is corn steep liquor, which without concentration usually contains up to about 2 weight % phytic acid. Of course, the medium to be treated can optionally be concentrated in phytic acid prior to treatment. The preferred medium will exhibit a pH of about 1 to about 5, which can be either its natural pH or that after adjustment with acid, e.g. $H_2SO_4$ or HCl, to convert phytic acid salt to the free acid form. In this regard, when such pH adjustment is undertaken in preferred processes of the invention, the adjusting acid is added in amounts only up to those sufficient to convert any phytic acid salt derivatives present to their free phytic acid form (i.e. no excess adjusting acid is added). As to the polymer used, in contrast to the pre-functionalized ionic exchange resins taught in the past, e.g. in the work of Ogawa et al. and of Ledding et al. described above, the polymers of this invention are free base polymers having tertiary amine functions to adsorb the phytic acid or phytic acid salt. It has surprisingly been discovered that despite lacking the strong ion-exchange character and function of the previously-used polymers, the polymers of this invention adsorb the phytic acid or its salt with unexpected efficacy and capacity by acid-base interaction. Further, the preferred polymers have proven highly regenerable, a factor which is also essential for commercially attractive processes of this type. The tertiary amine functions of the polymer can be provided by N-heterocyclic or by N-aliphatic groups. For example, AMBERLYST® A-21 resin, available from Rohm and Haas, Philadelphia, Pa., can be used in the invention. This A-21 resin contains aliphatic tertiary amine functions. For additional information about this and other similar resins, reference can be made to the literature including that available from the manufacturer. See, e.g., "AMBERLYST® A-21: technical bulletin fluid process chemicals," Rohm and Haas, April 1977.

In more preferred polymers, the tertiary amine functions are pyridine functions, for example as occur in polyvinylpyridine polymers. Poly 2- and poly 4-vinylpyridine polymers have provided particular advantage in work to date, especially such polymers at least about 2% crosslinked, e.g. with divinylbenzene.

In this regard, preferred polymers thus far have included those available from Reilly Industries, Inc., Indianapolis, Ind., in the REILLEX™ polymer series. These are poly 2- and poly 4-vinylpyridine polymers crosslinked with commercially available divinylbenzene. For example, REILLEX™ 425 polymer is a copolymer of 4-vinylpyridine and 25% divinylbenzene, exhibiting good thermal stability up to high temperatures of about 250° C. or more. This REILLEX™ 425 polymer exhibits a hard, macroreticular resin bead form, and has been a favored polymer in work to date. Additional resins are also suitable, of course, including for instance other bead-form REILLEX™ polymers which are either 2% or 25% crosslinked poly 2- or poly 4-vinylpyridine macroreticular or gel resins. For additional information about these and other REILLEX™ polymers, reference can be made to the literature, including for instance that available from Reilly Industries, Inc. in the form of REILLEX™ Reports 1, 2 and 3, which are hereby incorporated by reference in all aspects relevant and material to the invention.

As to the mode of contacting the phytic acid-containing medium with the polymer, this can be done in any suitable manner as those practiced in the area will appreciate. For instance, either fixed, moving or fluidized bed systems can be used to provide batch, semi-continuous or continuous processes. A fixed bed is preferably alternately contacted with the medium and a desorbent, each of which can be passed upflow or downflow through the resin bed. In a preferred mode, two or more fixed beds are provided in a system appropriately constructed and valved to reversibly contact one bed with the medium and another with desorbent and/or materials for rinsing and/or regenerating the resin. In this manner, continuous recovery processes can be conducted. Other contacting systems, for example countercurrent moving bed or simulated moving bed systems, can also be used within the skill of the ordinary artisan.

The flow rate of the contacting step will depend upon equipment, processing and other engineering factors, but usually ranges from about 2 to at least about 20 bed volumes per hour (b.v./hr.), and in work to date has ranged from about 4 to about 6 b.v./hr. This contacting step is continued until the polymer is essentially saturated with the phytic acid or phytic acid salt, as can be readily determined by monitoring the phytic acid content of the influent and effluent to and from the polymer bed.

After the contacting step, the phytic acid-loaded polymer is preferably rinsed with an aqueous medium at a moderate flow rate, e.g. about 10 to about 15 bed volumes per hour. This rinse is preferably performed at about ambient temperatures (e.g. approximately 20°–25° C.) or below, and more preferably at cold temperatures of about 2°–15° C. or even lower, so long as no significant freezing of the medium occurs. The aqueous rinse medium is preferably weakly acidic (e.g. pH about 4–6), advantageously by containing dissolved $CO_2$. The volume of the rinse is typically about 1 or more bed volumes, more preferably that amount just necessary to at least substantially remove non-adsorbed impurities from the resin bed, e.g. about 1 to 2 bed volumes in applicants' work so far.

In this embodiment, the phytic acid is desorbed from the polymer using any suitable agent therefor. For example, strong bases such as sodium hydroxide, e.g. 5% or more NaOH solutions, can be used, in which case the material is recovered as its sodium salt. The desorbent is advantageously passed through the polymer bed at a flow rate of about 6 to 12 bed volumes per hour. As to the volume of desorbent material used, this will vary, of course, with the particular adsorbent, desorbent, adsorbed materials and other factors involved. In preferred processes, about 4 to 8 bed volumes of desorbent have been employed.

In another preferred feature of the invention, an acid stronger than phytic acid, for instance a mineral acid solution (e.g. sulfuric acid) can effectively be used as a desorbent. When such an acid desorbent is employed, it effectively displaces phytic acid on the resin. From this desorbing step, a phytic acid fraction substantially free from contamination by the stronger acid is recovered, preferably containing 5% by weight or less of the stronger acid, more preferably 1% or less. This can be accomplished, for example, by monitoring the pH of the effluent, and discontinuing the flow of desorbent when the effluent pH drops to a point indicating significant presence of the stronger acid. For example, using 10% sulfuric acid solution as desorbent, the desorbent flow is preferably discontinued when the effluent pH drops below about 1.

As indicated above, in a preferred mode of this embodiment, the medium to be treated contains both phytic and lactic acid. Again, this medium is contacted with a solid-phase free base polymer having tertiary amine functions. A fraction predominant in phytic acid product, and a separate fraction predominant in lactic acid product, are then recovered from the polymer. The separate fractions are then preferably concentrated in their respective predominant products. This process thus enables effective and convenient winning of two highly valuable materials from the medium.

As before, the preferred medium for this embodiment is corn steep liquor which, in addition to containing phytic acid, also contains about 1% or more lactic acid prior to any concentration. Polymers employed, mode of contacting, desorption, rinse and other preferred parameters for this embodiment are similar to those set forth above, as modified or expanded by the following discussion.

Single or multiple columns containing resin beds can be used to provide processes in accordance with this mode. For instance, the medium containing phytic acid and lactic acid can be passed through a single column as in Example 2 below. The free base polymer will preferentially bind the phytic acid over the lactic acid, and thus the effluent will be rich in lactic acid while the adsorbed material on the resin will at least predominantly comprise phytic acid. The loaded polymer can then be treated with a desorbent to obtain a separate fraction predominant in the phytic acid. In this regard, the term "predominant in phytic acid" is intended to mean that the fraction contains more moles of phytic acid than lactic acid. Of course, then, "predominant in lactic acid" means the fraction contains more moles lactic acid than phytic acid. Favored are processes in which the medium contains the predominating material in at least twice the molar amount of the other material, and more preferably at least ten times the molar amount. As an example, the preferred work illustrated in Example 2 below achieved a fraction having a lactic acid/phytic acid molar ratio of greater than 200:1 (Fraction 1), and a phytic acid-containing fraction in which no lactic acid was detected (Fraction 3). This and other work by applicants has demonstrated the highly advantageous recoveries and separations achieved by this preferred process and highlighted the magnitude of their discovery.

In another preferred process mode, the medium is passed in series through a plurality of columns containing the polymer. In this manner, columns toward the beginning of the series will adsorb predominantly the phytic acid, and those later in the series will adsorb predominantly the lactic acid. Fractions can then be obtained from the respective columns which predominate in either the lactic acid or the phytic acid. In a preferred feature, a column or columns central in a series (i.e. having at least one column before and after) and containing substantial amounts of both lactic acid and phytic acid can go untreated, and simply be used at or near the beginning of the series in a subsequent run. These columns will then of course become rich in the phytic acid as lactic acid is displaced, carried downstream and for example adsorbed on a subsequent column. As such, fractions very highly predominant in the respective desired materials can be obtained. For instance, in Example 3 below, Fraction 1 exhibited a lactic acid/phytic acid ratio of about 132:1, and Fraction 3 exhibited a phytic acid/lactic acid ratio of greater than 20:1.

The phytic acid can be desorbed from the polymers as described above. Lactic acid can be desorbed using conventional processes, for instance using polar organic solvents such as alcohols (e.g. methanol), ketones, carboxylic esters, base (e.g., aqueous NaOH or $NH_3$), etc. However, in one preferred feature of the invention, the lactic acid is desorbed from a preferred pyridine-containing polymer using hot water at a temperature of about 75° C. or above, and more preferably about 85° to 100° C. Higher temperatures can also be used, for instance up to about 150° C. or more using steam and/or under pressure. By this discovery a greatly simplified product workup can be achieved, as compared to that incurred using known desorptions employing polar organic materials such as methanol.

In another favored process, a polymer bed containing adsorbed phytic acid as well as lactic acid can be subjected to a selective desorption treatment to separate the materials. First, the lactic acid is desorbed using hot water as described above. During this procedure, no significant amounts of phytic acid are removed from the polymer. As such, the polymer can then be treated with desorbents effective to remove the phytic acid (e.g. as described above), and thereby separate fractions predominant in phytic acid and lactic acid, respectively, can be obtained.

As with phytic acid, the applicants have discovered that lactic acid can also be advantageously desorbed from a free base polymer having tertiary amine groups, using a stronger acid, for instance desirably $H_2SO_4$ or HCl. In this case, a lactic acid-containing fraction substantially free from contamination by the stronger acid is recovered. Preferably, a lactic acid fraction containing 5% by weight or less of the stronger acid is recovered, more preferably 1% or less. Again, the flow of desorbent can be continued and a lactic acid fraction collected until a drop in the effluent pH indicates significant presence of the stronger acid. For instance, using 5% $H_2SO_4$ or HCl, the desorbent can be passed until the effluent pH drops below about 2. In preferred work thus far, at least about 75% of the lactic acid loaded on the polymer can be removed prior to any significant presence of the stronger acid in the effluent.

The fractions obtained in this embodiment can be conventionally processed to obtain the phytic acid and lactic acid. Preferably, these fractions are concentrated, and the phytic acid predominant fraction treated so as to hydrolyze this material to inositol.

As indicated, still another preferred embodiment of the invention relates to a process for obtaining inositol. This process includes the step of hydrolyzing phytic acid while adsorbed on a solid-phase free base polymer having pyridine functions, to thereby form inositol. Thus, in this embodiment inositol is recovered directly from the resin instead of recovering phytic acid which is subsequently hydrolyzed. The phytic acid-loaded resin is preferably but not necessarily one obtained as in the preferred embodiments described above. The hydrolysis will typically occur at temperatures of about 100° to about 180° C. or more, and preferably at superatmospheric pressures, e.g. at the autogenous pressure created by heating the loaded resin in aqueous medium in a sealed vessel such as an autoclave. Accordingly, an extraordinarily convenient process for obtaining inositol is provided, not requiring desorption of phytic acid and then subsequent conversion to inositol. Further, and importantly, the applicants have found that the preferred pyridine polymers employed are highly regenerable, as further described in Example 7 below.

In order to promote a further understanding of the invention and its preferred features and advantages, the following specific Examples are provided. It will be understood that these Examples are intended to be illustrative and not restrictive in character, and that all changes and modifications that come within the spirit of the invention are desired to be protected.

In the Examples, percents given are percents by weight unless otherwise specified or suggested in context. The aqueous solutions of phytic acid or salts of phytic acid obtained in the Examples below were analyzed by HPLC. Samples containing sodium phytate were acidified before analysis. Further, although sometimes recovered from the columns as its sodium salt, quantities of phytic acid are reported as grams of the free acid.

EXAMPLE 1

Removal of Phytic Acid From Medium Using Free Base Pyridine Polymer

A 1 inch inner diameter ("I.D.") glass column was packed with an aqueous slurry of REILLEX™ HP polymer available from Reilly Industries, Inc. of Indianapolis, Ind. Upon settling, the resin bed's volume was 23 mL. After removing water from the column until the liquid level was just above the resin, a 2% solution of phytic acid (at its natural pH, approx. 3) was passed through the resin bed at 6 to 10 bed volumes/hour and the conductivity of the effluent monitored. After ten bed volumes were passed through the column, the conductivity measurements indicated that the influent and effluent phytic acid concentrations were equal. This was taken as the saturation point of the resin. The column was rinsed with 2 bed volumes of cold (2° C.) water saturated with $CO_2$, whereafter a 5% solution of sodium hydroxide was passed through the resin to remove phytic acid as its sodium salt. One hundred and twenty milliliters of basic effluent were collected and analyzed by HPLC. A total of 3.4 g of phytic acid (its sodium salt) were recovered.

EXAMPLE 2

Separation of Phytic and Lactic Acids With Single Column

An aqueous slurry containing 80 mL of REILLEX™ 425 polymer (26.7 g of dry resin) was added to a 1 inch I.D. jacketed, glass column. The resin column was backwashed and the resin bed allowed to settle. A sample of corn steep liquor was filtered to remove suspended solids, and its pH adjusted to 1.8 with concentrated HCl. Upon analysis by HPLC, the solution was found to contain 0.8% phytic acid and 1.6% lactic acid. This solution was then passed through the resin bed at a flow-rate of 4 bed volumes/hour. The first 1,280 mL of effluent was collected as fraction 1. The column was rinsed with 1.5 bed volumes of cold (2° C.) water saturated with $CO_2$ and the rinse collected (120 mL) and combined with fraction 1. A 5% solution of sodium hydroxide was passed through the resin bed while monitoring the effluent pH. Fraction 2 (200 mL) was collected before the effluent became basic. The remaining effluent (120 mL) was collected as fraction 3. Upon rinsing with fresh water, the resin could be used again in another similar procedure. Table 1 below sets forth the phytic and lactic acid composition of each fraction as obtained by HPLC.

TABLE 1

| Fraction | Volume (mL) | Lactic Acid (g) | Phytic Acid (g) |
|---|---|---|---|
| 1 | 1400 | 16.7 | 0.6 |
| 2 | 200 | 0.8 | 3.9 |
| 3 | 120 | 0.0 | 5.8 |

EXAMPLE 3

Acid Separation by Selective Desorption From Column

An experiment was conducted to illustrate the ability to simultaneously recover and separate phytic and lactic acids by selectively desorbing them from a resin bed. As such, the procedure of Example 2 was repeated, except passage of the steep liquor through the columnswas stopped when equal amounts of lactic acid in the effluent and influent were observed. The resin bed was rinsed with cold $CO_2$ water as in Example 2, whereafter 120 mL of water was added to the column. A gentle flow of compressed air was passed upflow through the column to agitate the bed, and hot water was circulated through the column jacket until the internal column temperature reached 85° C. Thereafter, the flow of compressed air was stopped and the hot water in the column quickly drained. This step was repeated, and the two fractions thus collected were designated fraction 1 and fraction 2. Afterwards, the resin was backwashed with a minimum of water, the bed settled, and the liquid level adjusted to just above the resin. A 5% solution of sodium hydroxide was then passed through the resin as in Example 1 and another fraction collected as fraction 3. The phytic and lactic acid composition of the fractions, as determined by HPLC, are given in Table 2.

TABLE 2

| Fraction | Volume mL | Lactic Acid (g) | Phytic Acid (g) |
|---|---|---|---|
| 1 | 123 | 1.8 | 0.1 |
| 2 | 121 | 0.4 | 0.1 |
| 3 | 320 | .02 | 3.1 |

It was thus demonstrated that phytic and lactic acids could very effectively be simultaneously recovered and then separated in accordance with the invention. Further, after collection and analysis, fraction 3 was refluxed so as to hydrolyze phytic acid to inositol.

EXAMPLE 4

Multiple Column Selective Adsorption and Desorption of Lactic and Phytic Acids

A series of three columns, each containing about 80 mL of resin, was prepared as in Example 2. Corn steep liquor, also prepared as in Example 2, was passed through the three columns in series. When the third column in the series was saturated with lactic acid, flow was stopped, and all three columns were rinsed in series with cold $CO_2$ water as before. The first and third columns were then isolated and treated separately as follows:

Column 1: The resin in this column was rinsed with 3 bed volumes of 5% sodium hydroxide as in the Examples above, and the neutral and basic fractions collected. The two fractions were combined to give 250 mL of solution that contained 9.4 g of phytic acid and 1.1 g of lactic acid.

Column 3: The resin in column 3 was slurried with 140 mL of water and agitated with an upflow stream of compressed air. Hot water was circulated through the column jacket until the internal column temperature reached 90° C. The flow of air was stopped and, after the bed settled, the hot water quickly drained from the column. This hot water desorption procedure was repeated to give a second fraction. The two fractions were combined to give 286 mL of solution containing 3.2 g of lactic acid and less than 0.1 g of phytic acid.

Nothing was removed from column 2, which becomes column 1 in a subsequent cycle followed by the two freshly regenerated columns. In this manner, a highly effective recovery and separation process is performed, thus advantageously obtaining two valuable materials from the steep liquor.

EXAMPLE 5

Lactic and Phytic Acid Desorption with Strong Acid

The adsorption and rinse procedures of Example 4 were repeated and columns 1 and 3 again isolated. Columns 1 and 3 were then treated as follows:

Column 1: A 10% solution of sulfuric acid was prepared and passed through the resin bed in column 1. The pH of the column effluent was monitored. After the pH dropped to 0.6, flow was discontinued. HPLC analysis of the solution indicated that it contained 10.1 g of phytic acid and very little lactic acid. The solution remaining after analysis was refluxed for 18 hours to effect the hydrolysis of phytic acid to inositol. The resin in Column 1 was treated with either aqueous sodium hydroxide or ammonia and could then be used again.

Column 3: A 5% solution of HCl was prepared and passed through the resin in column 3. The pH of the effluent was monitored. Two fractions were collected. Fraction 1 was collected until the pH of the column effluent dropped below 2. Fraction 2 was collected thereafter. Upon analysis, fraction 1 was shown to contain 2.9 g lactic acid, and fraction 2 0.4 g lactic acid, each containing little phytic acid. The lactic acid in fraction 1 can be recovered as an 80% solution by decolorization and concentration. The pH of the second fraction is preferably adjusted to between 1.8 and 4.0, and processed with a subsequent portion of corn steep liquor to recover its lactic acid component.

EXAMPLE 6

Recovery of Phytic and Lactic Acid Using Resin With N-Aliphatic Tertiary Amine Functions A series of three columns, each containing about 80mL of Amberlyst A-21 instead of a crosslinked polyvinylpyridine were prepared and assembled as described in Example 4. Corn steep liquor was prepared and passed through the three resin columns as in this earlier experiment until the third column was saturated with lactic acid. The first and third columns were isolated, rinsed with cold water, and treated as follows:

Column 1: The resin in this column was rinsed with 3 bed volumes of 5% sodium hydroxide and then 1 bed volume of water. The rinse water was combined with the basic solution to give 310 mL of solution that contained 8.4 g of phytic acid (as sodium phytate) and 0.6 g of lactic acid (as sodium lactate).

Column 3: The resin in column 3 was rinsed with 10% sulfuric acid and a major fraction collected until a significant drop in the pH was observed. The major fraction contained 2.9 g of lactic acid and only a minor amount of sulfuric acid. The last acidic fraction of lactic acid can be recycled into fresh corn steep liquor upon adjustment of its pH to about 3 with aqueous base. The resin was reused after passing aqueous sodium hydroxide or ammonia through the column followed with a water rinse.

Also, in separate experiments the lactic acid was removed from the third column with aqueous sodium hydroxide or ammonia. In this case, a major fraction was collected until the pH increased significantly. Upon treatment with aqueous acid to adjust the pH to about 3, later fractions containing small amounts of sodium or ammonium lactate can be combined with fresh corn steep liquor and these smaller quantities of lactic acid recovered.

EXAMPLE 7

Direct Recovery of Inositol from Resin

In another feature of the invention, inositol can be recovered directly by hydrolysis of phytic acid or phytic acid salt while on the resin. To illustrate this, to a 40% aqueous phytic acid solution were added 143.7 g of REILLEX™ 425 polymer, which from earlier experimentation was determined to be sufficient to adsorb 28 g of phytic acid. This resin slurry was then treated at 180° C. for 3 hours under pressure in an autoclave. Upon analysis, complete hydrolysis of the phytic acid to inositol was shown (yield, 93% crude and 91% after carbon treatment). Inositol was isolated by distilling off the water from the aqueous layer and stirring the residue with methanol and acetone. The aqueous layer was obtained from the reaction mixture by filtering off the resin. The resin retained all the phosphoric acid formed during the hydrolysis of the phosphate ester. The regeneration of the 425 resin and the formation of a phosphate can then be accomplished by treatment with base. Analogous results are obtained where the adsorbed species is phytin.

EXAMPLE 8

Steam Desorption of Lactic Acid

A steam desorption apparatus was constructed including a 1 ½ inch outer diameter stainless steel pipe about 20 inches long. The upper end of the pipe was fitted with a valved steam inlet port and a pressure gauge. The lower end was fitted with a pressure regulation valve. A 14-inch stainless steel water cooled condenser was also attached below the pressure regulation valve. A fine stainless steel wire mesh was positioned in the lower end of the pipe to hold the polymer within the pipe. The apparatus was attached to a pressure regulated high pressure steam line.

One liter of a 6% aqueous solution lactic acid was prepared. 59.52 grams (dry basis) REILLEX™425 polymer were added to the solution and the solution stirred for about 2 hours at ambient temperature. The polymer was filtered off and washed with 250 ml of 10° C. carbonated water. The filtrate was analyzed by titration, whereby it was determined that 6.84 grams of lactic acid had been loaded onto the polymer (e.g. acid loading=grams acid in original solution less grams acid in filtrate). The loaded polymer was then placed into the steam desorption apparatus (filling about ⅔ the volume of the pipe), and the outer surface of the apparatus was then heated with live steam. After this, steam was passed through the apparatus at 8–15 psig and a flow rate of about 6 bed volumes per hour (as measured by rate of liquid collection). 100 ml fractions were collected, and each was titrated with 0.1N NaOH. Upon analysis, it was determined that 4.50 g of lactic acid were recovered within the first 3 bed volumes of steam collected. This represents a 65.8% recovery of lactic acid from the polymer in the first 3 bed volumes, demonstrating the high efficacy of the steam desorption procedure.

What is claimed is:

1. A process for recovering phytic acid from a plant extract liquid medium containing phytin, comprising:

adding an acid to said plant extract liquid medium to convert the phytin to phytic acid;

after said adding, contacting the medium with a solid-phase free base polymer having tertiary amine functions to adsorb the phytic acid;

after said contacting, rinsing said polymer with an aqueous rinse medium; and after said rinsing desorbing the phytic acid from said polymer by passing an aqueous acid or an aqueous base over said polymer.

2. A process according to claim 1, wherein said medium contains phytin.

3. A process according to claim 1, wherein said medium contains phytic acid.

4. A process according to claim 1, wherein said medium is corn steep liquor.

5. A process according to claim 1, wherein said solid-phase free base polymer is a polyvinylpyridine polymer.

6. A process according to claim 5, comprising passing a desorbing agent over the polymer after said contacting step to desorb the phytic acid or phytic acid salt from the polymer and thereby form a desorbate containing the phytic acid or phytic acid salt.

7. A process according to claim 6, wherein said polyvinylpyridine polymer is a poly 2- or poly 4-vinylpyridine polymer.

8. A process according to claim 7, wherein said poly 2- or poly 4-vinylpyridine polymer is a crosslinked polymer.

9. A process according to claim 8, wherein said poly 2or poly 4-vinylpyridine is a bead-form gel or macroreticular resin.

10. A process according to claim 9, wherein said poly 2- or poly 4-vinylpyridine polymer is crosslinked with divinylbenzene.

11. A process according to claim 10, wherein said poly 2- or poly 4-vinylpyridine polymer is at least about 2% crosslinked with divinylbenzene.

12. A process according to claim 11, wherein said polyvinylpyridine polymer is a poly 2-vinylpyridine polymer.

13. A process according to claim 11, wherein said polyvinylpyridine polymer is a poly 4-vinylpyridine polymer.

14. A process according to claim 11, wherein said poly 2- or poly 4-vinylpyridine polymer is a gel resin.

15. A process according to claim 11, wherein said poly 2- or poly 4-vinylpyridine polymer is a macroreticular resin.

16. A process according to claim 11, comprising increasing the concentration of the phytic acid or phytic acid salt in said desorbate.

17. A process according to claim 16, comprising hydrolyzing the phytic acid or phytic acid salt to inositol.

18. A process according to claim 17, wherein during said contacting said medium has a pH of about 1 to about 5.

19. A process according to claim 18, wherein said medium is acidified to convert phytin to phytic acid prior to said contacting.

20. A process according to claim 1, wherein said contacting is by a fixed or fluidized bed of said polymer.

21. A process according to claim 20, wherein said aqueous rinse medium contains $CO_2$.

22. A process according to claim 20, wherein said polymer is poly 4-vinylpyridine crosslinked with about 25% divinylbenzene.

23. A process according to claim 22, wherein during said contacting said medium contains about 1 to 5 percent by weight phytic acid.

24. A process according to claim 23, wherein said desorbing agent is aqueous sodium hydroxide and a sodium salt of phytic acid is recovered in said desorbate.

25. A process according to claim 20, wherein said desorbing agent is an acid stronger than phytic acid, and wherein said desorbate is free from contamination by the stronger acid.

26. A process according to claim 1, wherein the medium also contains lactic acid, and also comprising recovering from the polymer a fraction predominant in phytic acid or phytic acid salt and another fraction predominant in lactic acid.

27. A process according to claim 26, wherein said recovering includes passing said medium through said polymer to selectively adsorb phytic acid on the polymer, collecting the effluent from said passing which is predominant in lactic acid, and desorbing the phytic acid or a phytic acid salt from the polymer.

28. A process according to claim 27, wherein said recovering includes adsorbing both phytic acid and lactic acid on the polymer, and thereafter selectively desorbing the lactic acid and the phytic acid or a phytic acid salt from the polymer.

29. A process for recovering lactic acid from a liquid medium containing lactic acid, comprising:

contacting the medium with a solid-phase free base polymer having tertiary amine functions to adsorb the lactic acid, said contacting being continued until said polymer is substantially saturated with lactic acid;

after said contacting, rinsing said polymer with an aqueous rinse medium;

after said rinsing, desorbing said lactic acid by displacement on the polymer with a stronger acid by passing an aqueous solution of a stronger acid over the polymer; and recovering from said desorbing step a desorbed fraction consisting essentially of an aqueous lactic acid solution substantially free from contamination by the stronger acid.

30. A process for recovering lactic acid from a liquid medium containing lactic acid, comprising:

contacting the medium with an amount of solid-phase, divinylbenzene-crosslinked free base form polymer having tertiary amine groups to adsorb the lactic acid, said contacting being at a first temperature and being continued until said amount of solid-phase, divinylbenzene-crosslinked free base form polymer is substantially saturated with lactic acid;

after said contacting, rinsing said polymer with an aqueous rinse medium;

after said rinsing, desorbing the lactic acid from said polymer by passing hot water at a second temperature of at least about 75° C. over the polymer, said second temperature being higher than said first temperature; and recovering from said desorbing step a desorbed fraction consisting essentially of an aqueous solution of lactic acid.

31. A process for obtaining inositol, comprising hydrolyzing phytic acid or phytic acid salt while adsorbed on a solid-phase free base polymer having tertiary amine functions to form inositol, and recovering said inositol.

* * * * *

UNITED STATES PATENT AND TRADEMARK OFFICE
CERTIFICATE OF CORRECTION

PATENT NO. : 5,574,180
DATED : November 12, 1996
INVENTOR(S) : Donald McQuigg et al.

It is certified that error appears in the above-identified patent and that said Letters Patent is hereby corrected as shown below:

In col. 3, line 44, please delete "leachares" and insert in lieu thereof --leachates--.

In col. 7, line 2, please delete "call" and insert in lieu thereof --can--.

In col. 9, line 26, please delete "columnswas" and insert in lieu thereof --column was--.

In column 12, line 48, please delete "2or" and insert in lieu thereof --2- or--.

Signed and Sealed this

Twelfth Day of May, 1998

Attest:

BRUCE LEHMAN

Attesting Officer

Commissioner of Patents and Trademarks